(12) United States Patent
Kulstad et al.

(10) Patent No.: US 12,121,474 B2
(45) Date of Patent: *Oct. 22, 2024

(54) TEMPERATURE MANAGEMENT SYSTEMS

(71) Applicant: Advanced Cooling Therapy, Inc., Chicago, IL (US)

(72) Inventors: Erik Kulstad, Dallas, TX (US); Robin Drassler, Lemont, IL (US); Patrick Shanley, Chicago, IL (US); Melissa Naiman, Chicago, IL (US); Michael C. Garrett, Wilmette, IL (US); Frank E. Garrett, Jr., Barrington, IL (US)

(73) Assignee: Advanced Cooling Therapy, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/520,197

(22) Filed: Jul. 23, 2019

(65) Prior Publication Data

US 2019/0380867 A1 Dec. 19, 2019

Related U.S. Application Data

(63) Continuation of application No. 14/522,928, filed on Oct. 24, 2014, now Pat. No. 10,398,590.

(60) Provisional application No. 61/918,015, filed on Dec. 19, 2013, provisional application No. 61/895,499, filed on Oct. 25, 2013.

(51) Int. Cl.
 *A61F 7/10* (2006.01)
 *A61F 7/00* (2006.01)
 *A61F 7/12* (2006.01)

(52) U.S. Cl.
 CPC .............. *A61F 7/10* (2013.01); *A61F 7/0085* (2013.01); *A61F 7/12* (2013.01); *A61F 2007/0009* (2013.01); *A61F 2007/0056* (2013.01); *A61F 2007/0095* (2013.01)

(58) Field of Classification Search
 CPC ........................................................ A61F 7/12
 See application file for complete search history.

(56) References Cited

U.S. PATENT DOCUMENTS

| 4,867,344 A | 9/1989 | Bitterly |
| 5,154,198 A | 10/1992 | Allen |
| 5,895,418 A * | 4/1999 | Saringer ................. F25B 21/02 607/104 |
| 6,018,956 A | 2/2000 | Sakata et al. |
| 6,582,398 B1 | 6/2003 | Worthen et al. |
| 7,666,215 B2 | 2/2010 | Callister et al. |

(Continued)

FOREIGN PATENT DOCUMENTS

WO 2011103208 A2 8/2011

OTHER PUBLICATIONS

U.S. Appl. No. 14/522,928, filed Oct. 24, 2014.
International Search Report and Written Opinion for PCT/US2014/062118 dated Feb. 6, 2015 (9 pp.).

*Primary Examiner* — Kaitlyn E Smith
(74) *Attorney, Agent, or Firm* — Nutter McClennen & Fish LLP

(57) ABSTRACT

Systems and methods for managing patient temperature are disclosed. Temperature management systems that are suitable for an out-of-hospital setting are disclosed. Temperature management systems having a low power requirement are disclosed. Temperature management systems that include a disposable, single-use reservoir are disclosed.

17 Claims, 6 Drawing Sheets

(56) References Cited

U.S. PATENT DOCUMENTS

| | | |
|---|---|---|
| 8,231,664 B2 | 7/2012 | Kulstad et al. |
| 8,444,684 B2 | 5/2013 | Kulstad et al. |
| 8,475,509 B2 | 7/2013 | Dae |
| 8,523,929 B2 | 9/2013 | Kulstad et al. |
| 8,696,725 B2 | 4/2014 | Kulstad et al. |
| 10,398,590 B2 * | 9/2019 | Kulstad ............... A61F 7/0085 |
| 2001/0005791 A1 | 6/2001 | Ginsburg et al. |
| 2002/0032473 A1 | 3/2002 | Kushnir et al. |
| 2009/0043366 A1 | 2/2009 | Dae |
| 2009/0254083 A1 * | 10/2009 | Wallace ............. A61B 18/1492 606/41 |
| 2010/0121273 A1 | 5/2010 | Kochanek et al. |
| 2012/0265172 A1 | 10/2012 | Kulstad et al. |
| 2013/0006336 A1 | 1/2013 | Kulstad et al. |
| 2013/0030411 A1 | 1/2013 | Kreck et al. |
| 2013/0245729 A1 | 9/2013 | Edelman et al. |

\* cited by examiner

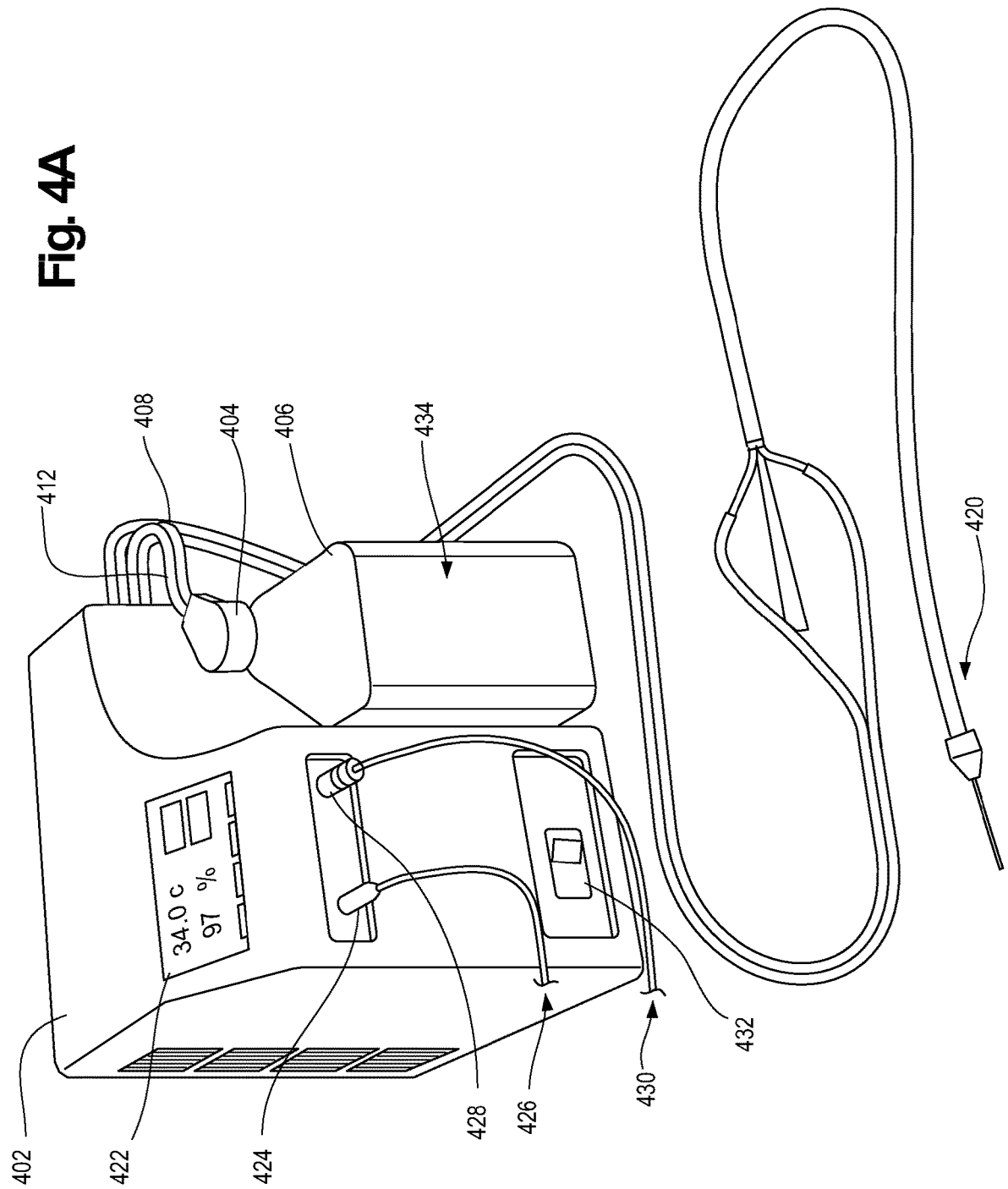

TEMPERATURE MANAGEMENT SYSTEMS

RELATED APPLICATIONS

This application claims the priority of U.S. nonprovisional application Ser. No. 14/522,928, filed on Oct. 24, 2014 which claims priority to U.S. provisional application Ser. No. 61/895,499, filed on Oct. 25, 2013, and Ser. No. 61/918,015, filed on Dec. 19, 2013, each of which are incorporated by reference in their entireties.

FIELD OF THE INVENTION

The present technology relates to devices, systems, and methods for managing core body temperature in a subject. In one aspect, the present technology relates to a device that delivers a heat transfer medium to a subject. In one aspect, the present technology relates to a temperature management system including a device that delivers a heat transfer medium to a subject. In one aspect, the present technology relates to a method of using a device that delivers a heat transfer medium to a subject to control core body temperature in the subject.

BACKGROUND OF THE INVENTION

Temperature management during the initial period after resuscitation from out-of-hospital cardiac arrest is an important factor in recovery. Induction of hypothermia improves outcomes in adults resuscitated from cardiac arrest. In addition, induction of hypothermia improves outcomes in neonates suffering from hypoxic ischemic encephalopathy. Temperature management may be of benefit in other conditions, such as spinal cord injury, stroke, meningitis and some subsets of traumatic brain injury. The general neuroprotective effects of mild therapeutic hypothermia mitigate both altitude and acceleration induced hypoxia, and more broadly, ischemia reperfusion injury. Moreover, temperature management in an operative setting may improve patient outcome and reduce adverse events. Nevertheless, therapeutic hypothermia is not readily available or used in all centers, let alone by emergency medical services ("EMS") personnel.

Currently available methods to control body temperature include both non-invasive techniques, such as surface cooling, and invasive techniques, such as intravascular cooling. For example, methods currently used to induce hypothermia require skin contact with blankets or pads, or intravascular access with catheter devices. These methods involve some limitations inherent in their approach, and surveys suggest that the technical difficulties involved in some methods may contribute to the underuse of treatment. Specific challenges with intravascular devices include the need to invasively access central circulation via needle puncture, the requirement for sterility in the placement of catheters, and the need for physician time and expertise for placement. Specific challenges with skin contact devices include the need to cover large critical areas of the skin and inefficiency in heat exchange across the skin which results in longer times to achieve goal temperature.

Commercially available heat exchangers are designed for circulation of coolant for medical applications such as blankets, catheters, and extremity pads. For example, the Medi-Therm III Hyper/Hypothermia machine (Gaymar Industries, Inc.) supplies temperature controlled water to a blanket. Model MTA7912 Medi-Therm III Hyper/Hypothermia machine weighs 68.6 kg when empty and includes a reservoir that holds 9.5 liters of distilled water. Model MTA7900 Medi-Therm III Hyper/Hypothermia machine weighs 55 kg when empty and includes separate hot and cold water reservoirs. Model MTA7912 Medi-Therm III Hyper/Hypothermia machine is reported to be 94 cm high×48 cm deep×36 cm wide. Model MTA7900 Medi-Therm III Hyper/Hypothermia machine is reported to be 94 cm high×46 cm deep×36 cm wide. In a poor cooling environment (e.g., 90° F. ambient temperatures), the Medi-Therm III Hyper/Hypothermia machine has a cooling capacity of greater than 630 W.

Accordingly, there is a need for temperature management systems, methods of operating a temperature management system, and methods of managing patient temperature that are portable, convenient, and easily employed by physicians, EMS personnel, and other health care providers. There is a need for temperature management systems, methods of operating a temperature management system, and methods of managing patient temperature that can be employed in an out-of-hospital setting by, for example, EMS personnel.

BRIEF SUMMARY OF THE INVENTION

At least one aspect of the present technology includes a temperature management system for managing patient temperature. In one aspect, the system is a system for inducing hypothermia. In one aspect, the system is a system for maintaining patient temperature at a desired target point or range. In certain embodiments, the temperature management system includes a heat transfer medium; a heat transfer medium reservoir; a heat exchanger; and a heat transfer device. In certain embodiments, the temperature management system includes an adapter for coupling the heat exchanger to the reservoir. In certain embodiments, the reservoir is a single use reservoir. In certain embodiments, the device is capable of being positioned within an orifice of a patient. For example, in certain embodiments, the heat transfer device is an esophageal heat transfer device.

At least one aspect of the present technology includes a system for managing patient temperature, the system including: (i) an esophageal heat transfer device; (ii) a heat transfer medium; (iii) a reservoir; and (iv) a heat exchanger. In certain embodiments, the system includes: (a) at least one processor; (b) at least one operator interface configured to provide input to the processor; and (c) at least one memory. The system is configured to: (1) receive an operator generated temperature setting and (2) control the temperature of the heat transfer medium and/or the flow rate of heat transfer medium through the esophageal heat transfer device.

At least one aspect of the present technology includes a system for managing patient temperature. In certain embodiments, the system includes a heat exchanger having sufficient cooling capacity to cause patient cooling to the desired temperature and/or at the desired rate when a heat transfer medium is circulated through a heat transfer device. In certain embodiments, the system includes a heat exchanger having sufficient heating capacity to cause patient warming to the desired temperature and/or at the desired rate when a heat transfer medium is circulated through a heat transfer device.

At least one aspect of the present technology includes a system for managing patient temperature, wherein the system has a low power requirement. In certain embodiments, the presently disclosed temperature management system has a relatively low power requirement compared to commercially available temperature management systems. In certain embodiments, the system includes a heat exchanger having a low power requirement. In certain embodiments, the presently disclosed heat exchanger has a relatively low power requirement compared to commercially available heat exchangers. For example, in certain embodiments, the energy requirements of the heat exchanger are about 72 Watts. In certain embodiments, the energy requirements of the heat exchanger are from about 72 Watts to about 216 Watts. In certain embodiments, the energy requirements of the heat exchanger are from less than 500 Watts; alternatively, less than 450 Watts; alternatively, less than 400 Watts; alternatively, less than 350 Watts; alternatively, less than 300 Watts; alternatively, less than 250 Watts; alternatively, less than 200 Watts; alternatively, less than 150 Watts; or alternatively, less than 100 Watts. The low power requirement aids in making the heat exchanger portable. The low power requirement allows the heat exchanger to be miniaturized in a portable hand-held device.

At least one aspect of the present technology includes a system for managing patient temperature, wherein the system includes a relatively small heat exchanger compared to commercially available heat exchangers. In certain embodiments, the heat exchanger described herein measures approximately 30 cm×15 cm×15 cm. As another example, the amount of space occupied by the heat exchanger described herein is less than 500 cm$^3$; alternatively less than 1000 cm$^3$; alternatively less than 2000 cm$^3$; alternatively less than 3000 cm$^3$; alternatively, less than 4000 cm$^3$; alternatively, less than 5000 cm$^3$; alternatively, less than 6000 cm$^3$; alternatively, less than 7000 cm$^3$; alternatively, less than 8000 cm$^3$; or alternatively, less than 9000 cm$^3$. As yet another example, the amount of space occupied by the heat exchanger described herein is about 250 cm$^3$; alternatively about 500 cm$^3$; alternatively about 1000 cm$^3$; alternatively about 2000 cm$^3$; alternatively about 3000 cm$^3$; alternatively, about 4000 cm$^3$; alternatively, about 5000 cm$^3$; alternatively, about 6000 cm$^3$; alternatively, about 7000 cm$^3$; alternatively, about 8000 cm$^3$; or alternatively, about 9000 cm$^3$. In certain embodiments, the heat exchanger weighs less than ten pounds; alternatively, less than nine pounds; alternatively, less than eight pounds; alternatively, less than seven pounds; alternatively, less than six pounds; alternatively, less than five pounds; alternatively, less than four pounds; alternatively, less than three pounds; alternatively, less than two pounds; or alternatively, less than one pound. In certain embodiments, the size of the presently described heat exchanger is suitable for many settings, including an emergency medicine setting that involves patient transport (e.g., by ambulance or helicopter).

At least one aspect of the present technology includes a system for managing patient temperature. In certain embodiments, the system includes at least one reservoir. In certain embodiments, the system includes at least one disposable reservoir. The at least one disposable reservoir is capable of storing a heat transfer medium. In certain embodiments, the at least one disposable reservoir can be coupled to a heat exchanger via an adapter. In certain embodiments, the system includes more than one reservoir for storing heat transfer medium. For example, in certain embodiments, the system includes a first reservoir for storing hot liquid and a second reservoir for storing cold liquid. As another example, in certain embodiments, the system includes a reservoir for storing an aqueous heat transfer medium and a second reservoir for storing a non-aqueous heat transfer medium.

At least one aspect of the present technology includes an adapter for coupling a heat exchanger to a reservoir. In certain embodiments, the adapter is a component of the heat exchanger. In certain embodiments, the adapter is a separate component that can be connected to the heat exchanger. In certain embodiments, the reservoir contains a heat transfer medium.

At least one aspect of the present technology includes a system for managing patient temperature. In certain embodiments, the system includes an esophageal cooling device. In certain embodiments, the system can be employed to maintain patient temperature, induce hypothermia, or treat hyperthermia via the circulation of a heat transfer medium from a heat exchanger device through the esophageal cooling device. In certain embodiments, warmed heat transfer medium is circulated through the esophageal cooling device via a pump in the heat exchanger. In certain embodiments, the heat exchanger has sufficient heating capacity to cause patient warming at the desired rate. In certain embodiments, cooled heat transfer medium is circulated through the esophageal cooling device via a pump in the heat exchanger. In certain embodiments, the heat exchanger has sufficient cooling capacity to cause patient cooling at the desired rate. In certain embodiments, the esophageal cooling device allows for gastric decompression.

At least one aspect of the present technology includes a highly portable patient temperature management system that is configured to control patient temperature. In certain embodiments, the system is configured to induce therapeutic hypothermia. In certain embodiments, the system is employed to mitigate the effects of hypoxia and ischemia reperfusion injury. In certain embodiments, the system is configured to maintain patient temperature at a desired target point or range. In certain embodiments, the temperature management system includes a heat transfer medium; a heat transfer medium reservoir; a heat exchanger; and a heat transfer device. In certain embodiments, the temperature management system includes an adapter for coupling the heat exchanger to the reservoir. In certain embodiments, the reservoir is a single use reservoir. In certain embodiments, the device is capable of being positioned within an orifice of a patient. For example, in certain embodiments, the heat transfer device is an esophageal heat transfer device. In certain embodiments, the esophageal heat transfer device is configured for placement via the nasogastric route. In certain embodiments, the esophageal heat transfer device is configured for placement via the orogastric route.

At least one aspect of the present technology includes a method of operating a temperature management system.

At least one aspect of the present technology includes a method of managing patient temperature. The method includes attaching a disposable reservoir to a heat exchanger, positioning a heat transfer device within a patient, and initiating flow of a heat transfer medium to the heat transfer device. In certain embodiments, the disposable reservoir contains the heat transfer medium. In certain embodiments, the disposable reservoir is attached to the heat exchanger via an adapter. In certain embodiments, the adapter includes at least one tube that provides a flow path for heat transfer medium between the reservoir and the heat exchanger. In certain embodiments, the adapter includes a screw-top or snap-on cap. In certain embodiments, the adapter includes a puncturer.

BRIEF DESCRIPTION OF SEVERAL VIEWS OF THE DRAWINGS

FIGS. 4A and 4B show a front and back view, respectively, of components of a temperature management system of another embodiment of the present technology.

DETAILED DESCRIPTION OF THE INVENTION

Figure 1:
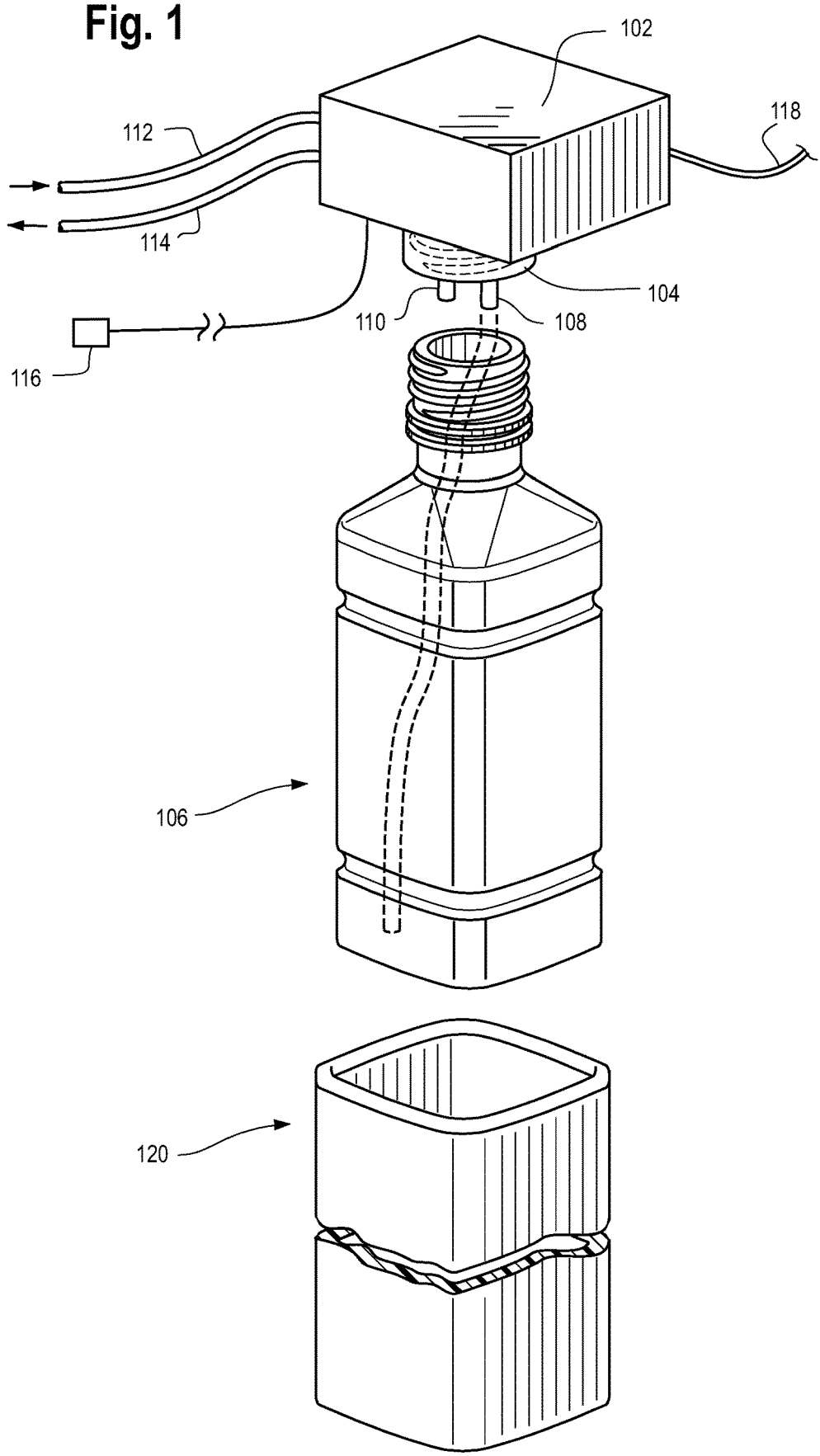
FIG. 1 depicts a schematic representation of components of a temperature management system of one embodiment of the present technology.

At least one aspect of the present technology includes a temperature management system. In certain embodiments, the temperature management system includes (a) a heat exchanger; (b) a heat transfer medium; (c) a reservoir; and (d) a heat transfer device. In certain embodiments, the temperature management system includes an adapter for coupling the heat exchanger to the reservoir. In certain embodiments, the reservoir is a single use reservoir. In certain embodiments, the temperature management system includes an auxiliary tube set for circulating the heat transfer medium between the heat exchanger and the heat transfer device. In certain embodiments, the heat transfer device is an esophageal heat transfer device.

At least one aspect of the present technology includes a temperature management system. The temperature management system comprises an esophageal heat transfer device including at least one lumen that provides a flow path for a heat transfer medium; at least one disposable reservoir containing the heat transfer medium; at least one heat exchanger configured to regulate temperature of the heat transfer medium; at least one adapter for coupling the disposable reservoir to the heat exchanger; at least one processor; at least one operator interface configured to provide input to the processor; at least one input device; and at least one memory device that stores a plurality of instructions. The instructions, when executed by the at least one processor, cause the at least one processor to: (i) operate with the at least one operator interface to receive a criterion for a feedback parameter; (ii) operate with the at least one input device to receive a measured value for the feedback parameter; (iii) determine whether the measured value satisfies the criterion; and (iv) adjust an operational setting of the system when the measured value does not satisfy the criterion. In certain embodiments, the feedback parameter is patient temperature. In certain embodiments, the feedback parameter is rate of patient temperature change. In certain embodiments, the feedback parameter is one or more of the following parameters: oxygen saturation, such as $SvO_2$, $StO_2$, or $SpO_2$; methemoglobin level; carboxyhemoglobin level; and/or variation in pulse oximetry plethysmographic waveform amplitude. In certain embodiments, the feedback parameter is one or more of a heat transfer medium flow rate; a heat transfer medium temperature; or a heat transfer medium temperature differential. In certain embodiments, the operational setting is a temperature of the heat transfer medium. In certain embodiments, the operational setting is a flow rate of the heat transfer medium. In certain embodiments, the operational setting is an operational speed of a variable speed motor that powers the heat exchanger.

At least one aspect of the present technology includes a heat exchanger. The heat exchanger is operable to cool or warm a heat transfer medium. The heat exchanger is operable to circulate the heat transfer medium through a patient circuit to control patient temperature. In certain embodiments, the patient circuit includes at least one lumen within an esophageal cooling device. In certain embodiments, the patient circuit includes a lumen or series of lumens within an esophageal cooling device.

In order to achieve desired temperature change per unit of time, the heat exchanger must have sufficient heating and cooling capacity. Surprisingly, the thermal requirements of patient warming and cooling via an esophageal cooling device are quite small compared to the capacity of known vapor pressure refrigeration units and resistive heaters.

In certain embodiments, about 72 W of cooling are required to achieve the targeted cooling rate. In certain embodiments, the heat exchanger has a cooling capacity of at least 72 W while circulating 4° C. coolant. In certain embodiments, about 100 W of cooling are required to achieve the targeted cooling rate. In certain embodiments, the heat exchanger has a cooling capacity of at least 100 W while circulating 4° C. coolant. In certain embodiments, about 125 W of cooling are required to achieve the targeted cooling rate. In certain embodiments, the heat exchanger has a cooling capacity of at least 125 W while circulating 4° C. coolant. In certain embodiments, about 150 W of cooling are required to achieve the targeted cooling rate. In certain embodiments, the heat exchanger has a cooling capacity of at least 150 W while circulating 4° C. coolant. In certain embodiments, about 175 W of cooling are required to achieve the targeted cooling rate. In certain embodiments, the heat exchanger has a cooling capacity of at least 175 W while circulating 4° C. coolant. In certain embodiments, about 200 W of cooling are required to achieve the targeted cooling rate. In certain embodiments, the heat exchanger has a cooling capacity of at least 200 W while circulating 4° C. coolant. In certain embodiments, the heat exchanger has a cooling capacity of at least 216 W while circulating 4° C. coolant. In certain embodiments, the heat exchanger has a cooling capacity between about 72 W and about 216 W while circulating 4° C. coolant. In certain embodiments, the heat exchanger has a cooling capacity between about 72 W and about 200 W while circulating 4° C. coolant. In certain embodiments, the heat exchanger has a cooling capacity between about 72 W and about 150 W while circulating 4° C. coolant. In certain embodiments, the heat exchanger has a cooling capacity between about 100 W and about 150 W while circulating 4° C. coolant. A correction factor can be applied to the cooling capacity to accommodate parasitic effects, and to ensure that the heat exchanger is not the limiting factor in device efficacy.

In certain embodiments, the targeted cooling rate is about 1.0° C./hour. In certain embodiments, the targeted cooling rate is less than 1.0° C./hour.

In certain embodiments, the heat exchanger consumes less than 500 W. In certain embodiments, the heat exchanger consumes less than 400 W. In certain embodiments, the heat exchanger consumes less than 500 W to achieve a cooling rate of 1.0° C./hour in a subject. In certain embodiments, the heat exchanger consumes less than 400 W to achieve a cooling rate of 1.0° C./hour in a subject. In certain embodiments, the heat exchanger consumes between about 72 W and about 450 W. In certain embodiments, the heat exchanger consumes between about 72 W and about 450 W to achieve a cooling rate of 1.0° C./hour in a subject. In certain embodiments, the heat exchanger consumes between about 300 W and about 400 W. In certain embodiments, the heat exchanger consumes between about 300 W and about 400 W to achieve a cooling rate of 1.0° C./hour in a subject. In certain embodiments, the heat exchanger consumes at least 216 W. In certain embodiments, the heat exchanger consumes at least 216 W to achieve a cooling rate of 1.0° C./hour in a subject. In certain embodiments, the subject has a mass of about 75 kg.

In certain embodiments, the heat exchanger consumes about 216 W. In certain embodiments, the heat exchanger consumes less than 216 W. In certain embodiments, the heat exchanger consumes about 200 W. In certain embodiments, the heat exchanger consumes less than 200 W. In certain embodiments, the heat exchanger consumes about 150 W. In certain embodiments, the heat exchanger consumes less than 150 W. In certain embodiments, the heat exchanger consumes about 125 W. In certain embodiments, the heat exchanger consumes less than 125 W. In certain embodiments, the heat exchanger consumes about 100 W. In certain embodiments, the heat exchanger consumes less than 100 W. In certain embodiments, the heat exchanger consumes about 72 W. In certain embodiments, the heat exchanger consumes about 72 W.

In certain embodiments, 7.2 W of warming are required to achieve the targeted warming rate. In certain embodiments, the heat exchanger has a warming capacity of at least 7.2 W while circulating 41° C. coolant. In certain embodiments, the heat exchanger has a warming capacity of at least 100 W while circulating 41° C. coolant. In certain embodiments, the heat exchanger has a warming capacity between about 7.2 W and about 100 W while circulating 41° C. coolant.

In certain embodiments, the targeted warming rate is at least 0.1° C./hour. In certain embodiments, the targeted warming rate is about 0.1° C./hour. In certain embodiments, the heat exchanger consumes about 100 W. In certain embodiments, the heat exchanger consumes less than 100 W. In certain embodiments, the heat exchanger consumes about 7.2 W. In certain embodiments, the heat exchanger consumes less than 7.2 W.

In certain embodiments, the heat exchanger is a chiller. The chiller is operative to cool a heat transfer medium. The chiller is also operative to circulate the heat transfer medium between the chiller and a cooling device via, for example, a coolant delivery circuit. The chilled heat transfer medium is delivered to the cooling device via a delivery lumen and is returned to the chiller via a return lumen. The spent coolant can be returned to the heat transfer medium reservoir, expelled from the system, or deposited into a separate collection reservoir.

In certain embodiments, the heat exchanger employs vapor cycle refrigeration. In certain embodiments, the heat exchanger includes a circuit containing a circulating refrigerant. The circuit can include an evaporator, a compressor, and an expansion valve. The circuit can also include a condenser. In the circuit, the refrigerant travels from the compressor to the expansion valve and then to the evaporator. The refrigerant is in thermal contact, but not fluid contact, with a heat transfer medium. When the refrigerant expands, it cools the heat transfer medium. The refrigerant can be, for example, ammonia, a chlorofluorocarbon ("CFC"), a hydrofluorocarbon ("HFC"), a hydrochlorofluorocarbon ("HCFC"), or a mixture thereof. A mixture of refrigerants can be an azeotropic mixture, a near-azeotropic mixture, or a non-azeotropic mixture.

In certain embodiments, the compressor is a small, high-performance rotary refrigeration compressor. In certain embodiments, the compressor is capable of producing about 300 W to about 400 W of cooling. In certain embodiments, the compressor weighs less than ten pounds; alternatively, less than nine pounds; alternatively, less than eight pounds; alternatively, less than seven pounds; alternatively, less than six pounds; alternatively, less than five pounds; alternatively, less than four pounds; alternatively, less than three pounds; alternatively, less than two pounds; or alternatively, less than one pound. In certain embodiments, the compressor is a brushless DC (BLDC) compressor. In certain embodiments, the compressor includes a variable speed motor. In certain embodiments, the variable speed motor is configured to operate between about 2,000 and about 6,500 rpm. In certain embodiments, the compressor is a miniature rotary compressor available from, for example, Aspen Compressor, LLC.

In certain embodiments, the heat exchanger includes a thermoelectric device, such as a Peltier device. At least a portion of the thermoelectric device is in thermal communication with a heat transfer medium.

In certain embodiments, the heat exchanger includes a pump for circulating heat transfer medium between the heat exchanger and a heat transfer device. For example, the pump can draw the heat transfer medium from a heat transfer medium reservoir and circulate the heat transfer medium between the heat exchanger and a heat transfer device via a heat transfer medium delivery circuit. The heat transfer medium can flow through a delivery lumen to the heat transfer device and return to the heat exchanger through a return lumen. In certain embodiments, the components of the heat exchanger that contact liquid are constructed from a corrosive-resistant material, such as titanium. In certain embodiments, the components of the heat exchanger that contact liquid are treated with an anti-corrosive agent.

In certain embodiments, the heat exchanger includes a connector for connecting to a power source, such as mains power (commonly 115 VAC/60 Hz or 220 VAC/50 Hz). In certain embodiments, the heat exchanger includes a connector for connecting to a power source, such as a docking station located within an ambulance, helicopter, or other transport vehicle. In certain embodiments, the heat exchanger includes an AC to DC converter.

In certain embodiments, the heat exchanger is Type BF ("body floating") rated to ensure that the patient is adequately isolated from voltages present on the mains power system. In certain embodiments, the heat exchanger is Type CF ("cardiac floating") rated to ensure that the patient is adequately isolated from voltages present on the mains power system. In certain embodiments, the isolation is provided within the heat exchanger.

In certain embodiments, the heat exchanger includes a DC motor. In certain embodiments, DC motor is a brushless DC motor. In certain embodiments, the DC motor is configured for variable speed operation. In certain embodiments, cooling capacity of the temperature management system can be regulated by changing the compressor speed.

In certain embodiments, the heat exchanger is powered by one or more batteries. In certain embodiments, the heat exchanger is powered by one or more regular or rechargeable batteries. In certain embodiments, the heat exchanger includes one or more regular or rechargeable batteries. In certain embodiments, the battery is a nickel metal hydride battery. In certain embodiments, the battery is a lithium polymer battery. In certain embodiments, the heat exchanger includes a military grade Lithium Metal Oxide battery, such as the Tadiran TLM1550M cell. In certain embodiments, the heat exchanger is powered by one or more reserve batteries that require activation to produce power. In certain embodiments, the heat exchanger is powered by one or more reserve batteries, such as a liquid reserve battery or a thermal battery. In certain embodiments, the heat exchanger includes at least one reserve battery. In certain embodiments, the heat exchanger includes a rechargeable power source.

In certain embodiments, the heat exchanger interfaces with an input device to sense and/or measure one or more physiological parameters. In certain embodiments, the one or more physiological parameters include patient temperature. In certain embodiments, the one or more physiological parameters include oxygen saturation, such as $SvO_2$, $StO_2$, or $SpO_2$; methemoglobin level; carboxyhemoglobin level; and/or variation in pulse oximetry plethysmographic waveform amplitude.

In certain embodiments, the heat exchanger interfaces with a patient temperature probe. The patient temperature probe can be a component of the heat exchanger or a separate device that is capable of being directly or indirectly coupled to the heat exchanger. Patient temperature probes are commercially available from, for example, Smiths Medical.

In certain embodiments, the heat exchanger includes a connection for a patient temperature probe. In certain embodiments, the heat exchanger includes a connection for a YSI-400 temperature probe. In certain embodiments, the heat exchanger includes a port to accept a patient temperature probe containing a standard ¼" phone plug connector.

Patient temperature probes are available for rectal, oral, vaginal, esophageal, bladder, gastric, or intravascular temperature measurement. If the heat transfer device is an esophageal heat transfer device, esophageal or oral temperature measurements may be confounded by the temperature of the circulating heat transfer medium. Thus, rectal, vaginal, bladder, gastric, or intravascular temperature measurement may be more appropriate where the heat transfer device is an esophageal heat transfer device. In certain embodiments, gastric temperature measurement can be employed.

In certain embodiments, the patient temperature probe includes a thermocouple. In certain embodiments, the patient temperature probe includes a thermistor. In certain embodiments, patient temperature measurement is accomplished using YSI400 series thermistors that convert temperature to electrical resistance. In certain embodiments, the patient temperature probe includes an infrared sensor. In certain embodiments, the patient temperature probe includes an integrated circuit temperature sensor. In certain embodiments, the patient temperature probe includes a resistance temperature detector ("RTD").

In certain embodiments, the patient temperature probe is disposable. In certain embodiments, the disposable patient temperature probe is a single use probe. In certain embodiments, the disposable patient temperature probe is a single patient use probe.

In certain embodiments, a patient temperature probe is placed in the patient's body. In certain embodiments, the patient temperature probe is placed in the gastrointestinal tract. In certain embodiments, the patient temperature probe is placed in the esophagus. In certain embodiments, the patient temperature probe is affixed to the heat transfer device. For example, in certain embodiments, the patient temperature probe is located at the distal end of an esophageal heat transfer device. The patient temperature probe converts patient temperature data into electronically readable signals that are transmitted to the heat exchanger. In certain embodiments, the patient temperature probe can be a YSI 400 Series temperature probe.

In certain embodiments, the heat exchanger interfaces with a pulse oximeter. The pulse oximeter can be a component of the heat exchanger or a separate device that is capable of being directly or indirectly coupled to the heat exchanger. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In certain embodiments, the pulse oximeter utilizes standard fingertip or surface probes.

In certain embodiments, one or more components of the temperature management system, such as the heat exchanger, are configured to communicate (via hardwire or wirelessly) with other components of the system. In certain embodiments, communication between or among components of the temperature management system occurs through one or more internal or external USB connections, HDMI connections, Bluetooth connections, NFC readers, radio frequency identifier (RFID) readers, and/or Wi-Fi connections. It should also be appreciated that, in certain embodiments, one or more components the temperature management system is configured to exchange data with other system devices via a connection to a data network. The network connection may be any suitable type of network connection, such as an Ethernet connection, a Wi-Fi connection to a local Wi-Fi network, 3G or 4G connections to a wireless carrier, or other wireless communication methods (such as a direct satellite connection). It should thus be appreciated that some or all of the data storage and/or data analysis functions of the temperature management system can be done remotely.

In certain embodiments, the heat exchanger is configured to send data to and/or receive data from other devices. For example, in certain embodiments, the heat exchanger is configured to acquire data related to patient parameters from other systems, such as the Propaq M series multi-parameter monitoring systems available from Zoll Medical Corporation or the Rainbow Pulse CO-Oximetry monitoring systems available from Masimo Corporation. As another example, the heat exchanger, in certain embodiments, is configured to push information about patient condition, (e.g., patient temperature, pressure, oxygen saturation, pH, heart rate, etc.) and/or alarm indications to a central computer or network of computers.

In certain embodiments, the heat exchanger is capable of being mounted on patient transfer device, such as a bed, stretcher, gurney, cart, or wheelchair. In certain embodiments, the heat exchanger includes a coupling unit for mounting the heat exchanger on the patient transfer device. In certain embodiments, the coupling unit includes at least one hook, bracket, or clamp.

At least one aspect of the present technology includes a heat transfer medium reservoir. The reservoir is operable to store heat transfer medium.

In certain embodiments, the heat transfer medium reservoir is provided with the heat exchanger. In other embodiments, the reservoir can be a standalone product.

In certain embodiments, the reservoir is a bottle. In certain embodiments, the bottle contains a biocompatible fluid. In certain embodiments, the bottle contains a liquid. In certain embodiments, the bottle contains a sterile liquid. In certain embodiments, the bottle contains an irrigation solution, such as sterile saline (0.9% sodium chloride solution) or sterile water. Such bottles are available from Baxter, for example.

In certain embodiments, the reservoir holds at least 1 liter of heat transfer medium. In certain embodiments, the reservoir holds between about 1 liter of heat transfer medium and about 3 liters of heat transfer medium. In certain embodiments, the reservoir holds about 1 liter of heat transfer medium; alternatively, about 1.5 liters of heat transfer medium; alternatively, about 2 liters of heat transfer medium; alternatively, about 2.5 liters of heat transfer medium; or alternatively, about 3 liters of heat transfer medium.

In certain embodiments, the reservoir is a cartridge. In certain embodiments, the cartridge is housed within the heat exchanger. In certain embodiments, the cartridge contains a sterile solution, such as sterile saline (0.9% sodium chloride solution) or sterile water.

In certain embodiments, the reservoir is disposable. In certain embodiments, the disposable reservoir is a single use reservoir. In certain embodiments, the disposable reservoir is a single patient use reservoir.

In certain embodiments, a single disposable reservoir is used throughout the entire period of temperature management for a given patient. In certain embodiments, the disposable reservoir is detached from the heat exchanger and discarded following the period of temperature management for a given patient.

In certain embodiments, a period of temperature management for a given patient spans a variety of locations and/or health care providers. For example, in certain embodiments, the temperature management system described herein may be employed by EMS personnel in an out-of-hospital setting; by a physician, nurse, or other health care provider at a level 2 cardiac resuscitation center ("CRC"); by transport personnel during ground or air transport from a level 2 CRC to a level 1 CRC; and/or by a physician, nurse, or other health care provider at a level 1 CRC. In certain embodiments, a period of temperature management for a given patient occurs in a single location.

In certain embodiments, a period of temperature management for a given patient has a duration of from about 1 hour to about 48 hours. In certain embodiments, the period of temperature management for a given patient includes a range or value that is at least 2 hours; alternatively, at least 4 hours; alternatively, at least 6 hours; alternatively, at least 12 hours; alternatively, at least 24 hours; or alternatively, at least 36 hours. In certain embodiments, the period of temperature management includes a range or value that is between about 1 hour and about 48 hours; alternatively, between about 4 hours and about 36 hours; or alternatively, between about 12 hours and about 24 hours.

In certain embodiments, the heat transfer medium is a biologically safe fluid. In certain embodiments, the heat transfer medium is substantially free of a biocide, including but not limited to a fungicide, an algaecide, and an antibacterial. In certain embodiments, the heat transfer medium is substantially free of chlorine.

At least one aspect of the present technology includes an adapter. The adapter is operable to couple a heat exchanger to a heat transfer medium reservoir.

In certain embodiments, the adapter is a component of the heat exchanger. In other embodiments, the adapter is a separate component that can be connected to the heat exchanger. For example, the adapter can include a tube or set of tubes that are connectable to the heat exchanger.

In certain embodiments, the adapter includes a screw-top or snap-on cap. For example, the adapter can be configured to be attached to a bottle. In certain embodiments, the adapter includes threads arranged to provide a threaded connection with the source of irrigation fluid.

In certain embodiments, the adapter includes a seal. In certain embodiments, the adapter includes a compression seal, grommet, O-ring, sealing membrane, gasket, or any like sealing component. In certain embodiments, the adapter includes a compression seal. In certain embodiments, the adapter includes a manually activated locking device. In certain embodiments, the manually activated locking device includes a toggle switch that loosens and/or tightens a compression seal. In certain embodiments, the adapter includes a snap-on cap, a compression seal, and a toggle switch that loosens and/or tightens the compression seal.

In certain embodiments, the adapter includes a puncturer. The puncturer is operable to access a reservoir by puncturing at least one barrier of the reservoir. In certain embodiments, the puncturer can be a spike. In certain embodiments, the puncturer includes a fluid channel. The fluid channel permits the heat transfer fluid to flow out of the reservoir.

In certain embodiments, the adapter includes an intake tube. In certain embodiments, the intake tube is coupled to the heat exchanger. In certain embodiments, the intake tube contacts heat transfer medium in the reservoir, thereby providing a flow path for heat transfer medium. In certain embodiments, the intake tube is configured to extend to the depth of the reservoir. In certain embodiments, the heat transfer medium flows through a lumen of the intake tube to the heat exchanger.

In certain embodiments, the adapter includes an output tube. In certain embodiments, the output tube is coupled to the heat exchanger. In certain embodiments, heat transfer medium returns to the reservoir through a lumen of the output tube.

At least one aspect of the present technology includes an auxiliary tube set for circulating a heat transfer medium between the heat exchanger and the heat transfer device. In certain embodiments, the heat transfer device includes an esophageal cooling device. For example, the heat exchanger and the esophageal heat transfer device are in fluid communication via the auxiliary tube set. In certain embodiments, the tube set includes a supply tube that interfaces to the heat exchanger on one end and the esophageal cooling device on the other end. The supply tube allows coolant to flow from the heat exchanger to the esophageal cooling device. In certain embodiments, the tube set includes a return tube that interfaces to the heat exchanger on one end and the esophageal cooling device on the other end. The return tube allows spent coolant to flow from the esophageal cooling device back to the heat exchanger. In certain embodiments, the supply tube has a length between about 2 feet and about 12. In certain embodiments, the supply tube is about 2 feet; alternatively, about 3 feet; alternatively, about 4 feet; alternatively, about 5 feet; alternatively, about 6 feet; alternatively, about 7 feet; alternatively, about 8 feet; alternatively, about 9 feet; alternatively, about 10 feet; alternatively, about 11 feet; or alternatively, about 12 feet. In certain embodiments, the return tube has a length between about 2 feet and about 12. In certain embodiments, the return tube is about 2 feet; alternatively, about 3 feet; alternatively, about 4 feet; alternatively, about 5 feet; alternatively, about 6 feet; alternatively, about 7 feet; alternatively, about 8 feet; alternatively, about 9 feet; alternatively, about 10 feet; alternatively, about 11 feet; or alternatively, about 12 feet.

At least one aspect of the present technology includes at least one sensor for detecting parameters of the heat transfer medium. In certain embodiments, the at least one sensor is disposed on the heat exchanger. In certain embodiments, the at least one sensor is disposed on the reservoir. In certain embodiments, the at least one sensor is disposed on the auxiliary tube set. In certain embodiments, the at least one sensor is disposed on a return tube of the auxiliary tube set. In certain embodiments, the at least one sensor is disposed on a supply tube of the auxiliary tube set. In certain embodiments, one sensor is disposed on a supply tube of the auxiliary tube set and another sensor is disposed on a return tube of the auxiliary tube set. In certain embodiments, the at least one sensor includes a temperature sensor. In certain embodiments, the at least one sensor includes a pressure sensor. Such sensors allow for the temperature and/or pressure of the heat transfer medium to be monitored as it circulates between the reservoir, the heat exchanger, and the heat transfer device. In certain embodiments, at least one temperature sensor generates a temperature signal related to the temperature of the heat transfer medium.

At least one aspect of the present technology includes a heat transfer device. The heat transfer device is operable to be placed in a patient orifice. The heat transfer device is operable to transfer heat to or from the patient.

In some embodiments, the heat transfer device is an esophageal heat transfer device as described in U.S. Pat. Nos. 8,231,664; 8,444,684; and 8,523,929 and US Patent Application Publication Nos. 2011/0125053, 2012/0265172, and 2013/0006336, the contents of which are hereby incorporated by reference in their entireties.

The heat transfer device may include a balloon or partially inflatable lumen. Alternatively, in certain embodiments of the present invention, the heat transfer portion of the heat transfer device does not include a balloon or partially inflatable lumen.

In certain embodiments, the esophageal heat transfer device includes an inflow lumen connected to a heat transfer medium input port and an outflow lumen connected to a heat transfer medium output port. The inflow lumen and outflow lumen are in fluid communication with each other. In certain embodiments, a volume of heat transfer medium is delivered to the esophageal heat transfer device and circulates through the esophageal heat transfer device. In certain embodiments, the esophageal heat transfer device holds less than about 0.1 liters of heat transfer medium. In certain embodiments, the esophageal heat transfer device holds between about 0.02 liters and about 0.1 liters of heat transfer medium. In certain embodiments, the esophageal heat transfer device holds about 0.1 liters; alternatively, about 0.09 liters; alternatively, about 0.08 liters; alternatively, about 0.07 liters; alternatively, about 0.06 liters; alternatively, about 0.05 liters; alternatively, about 0.04 liters; alternatively, about 0.03 liters; or alternatively, about 0.02 liters of heat transfer medium.

The heat transfer device may be, for example, a pharyngeoesophageal heat transfer device, an esophageal heat transfer device, an esophago-gastric heat transfer device, or a pharyngeoesophago-gastric heat transfer device. For example, an esophageal heat transfer device may include a heat transfer region of about twenty (20) centimeters. Alternatively, an esophago-gastric heat transfer device may include a heat transfer region of about forty (40) centimeters. As yet another alternative, a pharyngeoesophago-gastric heat transfer device may include a heat transfer region of about forty-five (45) to about fifty (50) centimeters. Heat transfer devices of the present technology can include heat transfer regions of about 22, about 24, about 26, about 28, about 30, about 32, about 34, about 36, about 38, about 40, about 42, about 44, about 46, about 48, about 50, about 52, about 54, about 56, about 58, about 60, about 62, about 64 about 66, about 68 or about 70 centimeters.

Heat transfer devices of the present technology can have a heat transfer region having a diameter of, for example, about 1.0 to about 2.0 centimeters. The diameter of the heat transfer region can be about 1.1, about 1.2, about 1.3, about 1.4, about 1.5, about 1.6, about 1.7, about 1.8, or about 1.9 centimeters. In certain embodiments, a heat transfer region of a heat transfer device of the present technology has a length of about 32 centimeters and a diameter of about 1.4 centimeters, giving a surface area of about 140 $cm^2$.

Increasing the length and/or circumference of the heat transfer region of the device, and therefore the surface area of the heat transfer region, improves the speed and efficiency at which the patient is cooled or heated (or re-warmed). In certain embodiments the heat transfer region can be about 15 $in^2$, about 20 $in^2$, about 25 $in^2$, 30 $in^2$, about 35 $in^2$, about 40 $in^2$, about 45 $in^2$, about 50 $cm^2$ about 60 $cm^2$, about 70 $cm^2$, about 80 $cm^2$, about 90 $cm^2$, about 100 $cm^2$, about 110 $cm^2$, about 120 $cm^2$, about 130 $cm^2$, about 140 $cm^2$, about 150 $cm^2$, about 160 $cm^2$, about 170 $cm^2$, about 180 $cm^2$, about 190 $cm^2$, about 200 $cm^2$, about 210 $cm^2$, about 220 $cm^2$, about 230 $cm^2$, about 240 $cm^2$, about 250 $cm^2$, about 260 $cm^2$, about 270 $cm^2$, about 280 $cm^2$, about 290 $cm^2$, about 300 $cm^2$, about 310 $cm^2$, about 320 $cm^2$, about 330 $cm^2$, about 340 $cm^2$, or about 350 $cm^2$.

In certain embodiments, the esophageal heat transfer device includes an inflow lumen connected to a heat transfer medium input port; a heat transfer region; an outflow lumen connected to a heat transfer medium output port; and a distal end configured for insertion into a nostril or mouth of a patient. Thus, in certain embodiments, the esophageal heat transfer device is orally or nasally inserted into the patient. In certain embodiments, the esophageal heat transfer device allows for gastric decompression. In certain embodiments, the esophageal heat transfer device is capable of receiving a separate gastric tube or gastric probe. In certain embodiments, the esophageal heat transfer device includes a gastric access tube capable of receiving the separate gastric tube or gastric probe. In certain embodiments, the gastric probe is a gastric temperature probe.

In certain embodiments, the esophageal heat transfer device improves cardiac output. In certain embodiments, the esophageal heat transfer device improves cardiac output during cardiopulmonary resuscitation ("CPR"). In certain embodiments, the esophageal heat transfer device adds support to the medial aspect of the heart, which helps reinforce the compression of the heart during the down stroke of CPR. In certain embodiments, the esophageal heat transfer device augments manual chest compressions delivered by, for example, EMS personnel.

In certain embodiments, the esophageal heat transfer device is an esophageal cooling device. In certain embodiments, the esophageal cooling device connects to standard hospital suction to provide gastric decompression. In certain embodiments, the esophageal cooling device includes three lumina: the two outermost lumina circulate coolant from the proximal end of the device to the distal end and back again to the proximal end; a central lumen is used for gastric decompression. In certain embodiments, the central lumen allows for the removal of gastric contents. In certain embodiments, the central lumen is defined by a central tube having one or more distal openings. In certain embodiments, the central tube is capable of being connected to a suction system. For example, in certain embodiments, the proximal end of the central tube is configured using a standard taper fitting for connection to hospital suction devices.

In certain embodiments, the temperature management system includes: (i) at least one processor; (ii) at least one operator interface configured to provide input to the processor; and (iii) at least one memory device.

The at least one processor is configured to communicate with, configured to access, and configured to exchange signals with at least one memory device. In certain embodiments, the processor can be a PID controller or may incorporate a PID controller.

The memory device is computer-readable storage media that stores software that is executed by the processor and which controls the operation of one or more components of the temperature management system, such as a heat exchanger. In various embodiments, the at least one memory device includes random access memory ("RAM"), which can include non-volatile RAM ("NVRAM"), magnetic RAM ("MRAM"), ferroelectric RAM ("FeRAM"), and other forms as commonly understood in the health care industry. In other embodiments, the at least one memory device includes read only memory ("ROM"). In certain embodiments, the at least one memory device includes flash memory and/or EEPROM (electrically erasable programmable read only memory). Any other suitable magnetic, optical, and/or semiconductor memory may operate in conjunction with the temperature management system disclosed herein. In certain embodiments, the memory device stores a plurality of instructions.

In certain embodiments, the at least one processor and the at least one memory device both reside within a cabinet that houses a component of the temperature management system. In other embodiments, at least one of the at least one processor and the at least one memory device reside outside of a cabinet that houses a component of the temperature management system.

In certain embodiments, the at least one operator interface is ruggedized. In certain embodiments, the at least one operator interface includes a graphics capable display device. In certain embodiments, the display device is fully viewable in sunlight and/or back lit for use in dark areas. In certain embodiments, the at least one operator interface includes a display device and one or more buttons. An operator can interact with the system through the at least one operator interface.

The at least one operator interface is communicably connected to the processor such that the processor is capable of receiving operator input. In certain embodiments, the at least one operator interface includes a control panel. The control panel includes one or more knobs or buttons that enable the operator to manipulate certain settings of one or more components of the temperature management system. In certain embodiments, the at least one operator interface includes a display device. The display device presents certain images and/or information to the use. For example, in certain embodiments, the display device presents patient temperature, heat transfer medium temperature, and/or heat transfer medium flow rate. In certain embodiments, the system enables the user to select between Fahrenheit and Celsius displays.

In certain embodiments, the display device is further configured to receive input from an operator. For example, in certain embodiments, the display device is configured as a touch-screen input device.

It should be appreciated that, in certain embodiments, the temperature management system of the present disclosure is configured to enable users to employ an operator interface to access the processor through the Internet or any other suitable data network, such as a mobile communications network, a local area network ("LAN"), or a wide area network ("WAN"). For example, in certain embodiments, the temperature management system includes a remote operator interface that enables an operator to provide input or view output from a remote location.

In certain embodiments, the temperature management system includes one or more remote computers. In certain embodiments, the remote computers are accessible through the internet. In certain embodiments, the system is configured implement data access through an embedded web server. In certain embodiments, the system is configured to communicate information to and/or from an external web server. In certain embodiments, communication between or among components of the temperature management system occurs through one or more internal or external USB connections, HDMI connections, Bluetooth connections, NFC readers, radio frequency identifier (RFID) readers, and/or Wi-Fi connections. It should also be appreciated that, in certain embodiments, one or more components the temperature management system is configured to exchange data with other system devices via a connection to a data network. The network connection may be any suitable type of network connection, such as an Ethernet connection, a Wi-Fi connection to a local Wi-Fi network, 3G or 4G connections to a wireless carrier, or other wireless communication methods (such as a direct satellite connection). It should thus be appreciated that some or all of the data storage and/or data analysis functions of the system can be done remotely. It should be appreciated that, in various embodiments, the system and the software applications running on the system are configured to function in an offline mode in the event that Internet access is unavailable for an unspecified length of time.

In certain embodiments, the temperature management system enables an operator to set a criterion for a measured physiological parameter, such as patient temperature. In certain embodiments, the temperature management system is configured to receive an operator generated criterion for a measured physiological parameter, such as patient temperature. In certain embodiments, the criterion is a target range. In certain embodiments, the criterion is a target value. For example, the system enables an operator to set a criterion for patient temperature. In certain embodiments, the criterion for patient temperature includes a range or value that is less than 37° C.; alternatively, less than 36° C.; alternatively, less than 35° C.; alternatively, less than 34° C.; alternatively, less than 33° C. In certain embodiments, the criterion for patient temperature includes a range or value that is between about 32° C. and about 37° C.; alternatively, between about 32° C. and about 36° C.; alternatively, between about 32° C. and about 35° C.; alternatively, between about 33° C. and about 36° C.; alternatively, between about 33° C. and about 35° C.; or alternatively, between about 33° C. and about 34° C.

In certain embodiments, the system enables one or more physiological parameters to be sensed or measured continuously. In certain embodiments, the system enables one or more physiological parameters to be sensed or measured in real time. In certain embodiments, system enables one or more physiological parameters to be sensed or measured at periodic intervals throughout the temperature management procedure.

In certain embodiments, the physiological parameter is patient temperature, pressure, oxygen saturation, pH, heart rate, Doppler signals, electromagnetic fluctuations, or chemical composition. For example, in certain embodiments, the temperature management system includes or incorporates electrochemical biosensors, or biological micro-electromechanical systems ("Bio-MEMS"), allowing lab-on-chip ("LOC") and incorporation of Micro Total Analysis Systems ("µTAS") analysis of biochemical composition of the physiological environment.

In certain embodiments, the temperature management system is configured to monitor oxygen content in the patient's blood. In certain embodiments, the temperature management system is configured to monitor hemoglobin, methemoglobin, and/or carboxyhemoglobin levels in the patient's blood. In certain embodiments, the temperature management system is configured to monitor pulse rate and perfusion information. In certain embodiments, the temperature management system is configured to monitor variations in perfusion. In certain embodiments, the temperature management system is configured to monitor variations in pulse oximetry plethysmographic waveform amplitude ("APOP"). In certain embodiments, the temperature management system is configured to display patient data on a display device.

In certain embodiments, the temperature management system is configured to monitor the patient's oxygen saturation ("$SO_2$"). In certain embodiments, the temperature management system is configured to monitor oxygen levels in the patient's blood or tissue. In certain embodiments, the temperature management system is configured to monitor carbon monoxide levels in the patient's blood or tissue. In certain embodiments, the temperature management system is configured to provide hypoxia monitoring. In certain embodiments, the temperature management system is configured to provide non-invasive hypoxia monitoring. In certain embodiments, the temperature management system is configured to monitor venous oxygen saturation ("$SvO_2$") or central venous oxygen saturation ("$ScvO_2$"). In certain embodiments, the temperature management system is configured to monitor tissue oxygen saturation ("$StO_2$"). In certain embodiments, the temperature management system is configured to monitor peripheral capillary oxygen saturation ("$SpO_2$").

In certain embodiments, the temperature management system is configured to detect hypoxia and/or monitor oxygen saturation. In certain embodiments, the temperature management system includes an integrated pulse oximeter. For example, in certain embodiments, the temperature management system includes a pulse oximeter that utilizes standard fingertip and surface probes. In certain embodiments, the temperature management system is configured to report measurements obtained via the pulse oximeter to an operator. In certain embodiments, the temperature management system is configured to alert the operator to measurements that fall outside of a specified range. In certain embodiments, the temperature management system is configured to enable the operator to set limits for the specified range.

In certain embodiments, one or more components of the temperature management system receive a criterion for determining whether a patient is hypoxic; receive a measured value for a patient parameter relating to hypoxia; and determine whether the measured value satisfies the criterion. In certain embodiments, one or more components of the temperature management system adjust an operational setting of the system when the measured value does not satisfy the criterion. In certain embodiments, one or more components of the temperature management system maintain an operational setting of the system when the measured value satisfies the criterion.

In certain embodiments, one or more components of the temperature management system receive a criterion for patient oxygen saturation; receive a measured value for actual patient oxygen saturation; and determine whether the actual patient oxygen saturation satisfies the criterion. In certain embodiments, one or more components of the temperature management system adjust an operational setting of the system when the actual patient oxygen saturation does not satisfy the criterion. In certain embodiments, one or more components of the temperature management system maintain an operational setting of the system when the actual patient oxygen saturation satisfies the criterion.

In certain embodiments, the temperature management system is configured to receive feedback from the patient. In certain embodiments, the patient feedback is patient temperature. In certain embodiments, the patient feedback is one or more of the following parameters: oxygen saturation such as $SvO_2$, $StO_2$, or $SpO_2$; methemoglobin level; carboxyhemoglobin level; and variation in pulse oximetry plethysmographic waveform amplitude.

In certain embodiments, one or more components of the temperature management system receive a criterion for patient temperature; receive a measured value for actual patient temperature; and determine whether the actual patient temperature satisfies the criterion. In certain embodiments, one or more components of the temperature management system adjust an operational setting of the system when the actual patient temperature does not satisfy the criterion. In certain embodiments, one or more components of the temperature management system maintain an operational setting of the system when the actual patient temperature satisfies the criterion.

In certain embodiments, the temperature management system is configured to adjust one or more operational parameters based on one or more physiological parameters of the patient. In certain embodiments, the physiological parameter is patient temperature. In certain embodiments, the physiological parameter is one or more of the following parameters: oxygen saturation such as $SvO_2$, $StO_2$, or $SpO_2$; methemoglobin level; carboxyhemoglobin level; and variation in pulse oximetry plethysmographic waveform amplitude.

In certain embodiments, the temperature management system is configured to receive feedback from one or more components of the system. In certain embodiments, the temperature management system is configured to monitor the temperature of the heat transfer medium. In certain embodiments, the temperature management system is configured to determine a heat transfer medium temperature differential ("$\Delta T_{HTM}$"). In certain embodiments, $\Delta T_{HTM}$ is determined by measuring the temperature of the heat transfer medium entering the heat transfer device ("$T_{inlet}$"), measuring the temperature of the heat transfer medium exiting the heat transfer device ("$T_{outlet}$"), and determining the difference between $T_{inlet}$ and $T_{outlet}$.

In certain embodiments, the temperature management system is configured to adjust one or more operational parameters based on feedback from one or more components of the system. For example, in certain embodiments, the temperature management system is configured to adjust compressor speed or pump output based on feedback from one or more components of the system. In certain embodiments, the temperature management system is configured to adjust compressor speed or pump output based on the temperature of the heat transfer medium. In certain embodiments, the temperature management system is configured to adjust compressor speed or pump output based on $\Delta T_{HTM}$. For example, in certain embodiments, the temperature management system is configured to reduce the compressor speed when $\Delta T_{HTM}$ is about 3, less than 3, about 2, less than 2, about 1, less than 1, or about 0. As another example, in certain embodiments, the temperature management system is configured to reduce the pump output when $\Delta T_{HTM}$ is about 3, less than 3, about 2, less than 2, about 1, less than 1, or about 0. In certain embodiments, the temperature management system is configured to reduce compressor speed or pump output when $\Delta T_{HTM}$ is about 0.

In certain embodiments, the temperature management system is configured to regulate the temperature and/or flow rate of the heat transfer medium. In certain embodiments, the temperature management system is configured to adjust coolant temperature or coolant flow rate based on patient temperature data. For example, in certain embodiments, a component of the system (e.g., the heat exchanger) receives input from a rectal temperature probe and adjusts the temperature of the heat transfer medium to obtain the desired target temperature and/or the desired rate of temperature change. In certain embodiments, the flow rate is at least 31 liters/hour.

In certain embodiments, the temperature management system is configured to adjust coolant temperature or coolant flow rate based on patient parameters. For example, in certain embodiments, the temperature management system is configured to adjust coolant temperature or coolant flow rate based on one or more of the following parameters: oxygen saturation such as $SvO_2$, $StO_2$, or $SpO_2$; methemoglobin level; carboxyhemoglobin level; and variation in pulse oximetry plethysmographic waveform amplitude.

In certain embodiments, the temperature management system includes a safety system. In certain embodiments, the safety system prevents flow of heat transfer medium when the temperature of the heat transfer medium is greater than 49° C.; alternatively, greater than 48° C.; alternatively, greater than 47° C.; alternatively, greater than 46° C.; alternatively, greater than 45° C.; alternatively, greater than 44° C.; alternatively, greater than 43° C.; or alternatively, greater than 42° C. In certain embodiments, the safety system prevents flow of heat transfer medium when the temperature of the heat transfer medium is less than 4° C.; alternatively, less than 3° C.; alternatively, less than 2° C.; alternatively, less than 1° C.; alternatively, less than 0° C.; alternatively, less than −1° C.; alternatively, less than −2° C.; alternatively, less than −3° C.; alternatively, less than −4° C.; alternatively, less than −5° C.; or alternatively, less than −6° C.

In certain embodiments, the temperature management system includes two patient temperature probes. In certain embodiments, the temperature management system includes a safety system based on the temperature differential between the two patient temperature probes. In certain embodiments, the safety system prevents flow of heat transfer medium when the differential between the two patient temperature probes exceeds a set value. In certain embodiments, the safety system is configured to alert the operator when the differential between the two patient temperature probes exceeds a set value.

In certain embodiments, the temperature management system is configured to regulate the temperature of the patient. For example, in certain embodiments, the system enables an operator to enter a target patient temperature. The system monitors actual patient temperature and, in the event that the target patient temperature is different from the actual patient temperature, adjusts the temperature and/or flow rate of the circulating coolant.

In certain embodiments, the temperature management system is configured to maintain the patient temperature between 33° C. and 37° C. For example, in certain embodiments, the temperature management system adjusts or maintains the temperature of the heat transfer medium to achieve the desired patient temperature. As another example, in certain embodiments, the temperature management system adjusts or maintains the temperature of the heat transfer medium to achieve the desired rate of patient temperature change over a period of time. As yet another example, in certain embodiments, the temperature management system adjusts or maintains the flow rate of heat transfer medium through the esophageal heat transfer device to achieve the desired patient temperature.

In certain embodiments, the temperature management system is configured to regulate the rate of patient temperature change. For example, in certain embodiments, the system enables multiple rates of patient temperature change, such as gradual, moderate, or rapid.

In certain embodiments, the temperature management system is configured to change the temperature of a patient without overshoot of more than 1° C. The rate of achieving a target temperature during induced hypothermia and the rate of rewarming a hypothermic patient may be fast or slow. For example, in certain embodiments, the temperature management system alters the rate of change of the patient's temperature by adjusting the temperature of the circulating coolant.

In certain embodiments, the system is configured to monitor patient temperature and alert the operator to patient temperature measurements that fall outside of a specified range. For example, in certain embodiments, the system is configured to monitor patient temperature and alert the operator if the patient temperature is below 29° C. or above 45° C.

In certain embodiments, the system is configured to monitor rate of patient temperature change and alert the operator if the rate of patient temperature change deviates from a specified range or value. For example, in certain embodiments, the system is configured to monitor the rate of patient temperature change and alert the operator if the rate of patient temperature change is below 1° C. per hour.

In certain embodiments, the temperature management system is configured to monitor the flow rate to detect system failures (e.g., flow stoppage due to occlusion, such as a pinched tube or hose). For example, in certain embodiments, the system includes a flow sensor that detects occlusion of flow. In certain embodiments, the system is configured to alert a healthcare provider of the system failure.

In certain embodiments, the temperature management system is configured to provide a visual or an audible alert or a combination of visual and audible alerts. For example, in certain embodiments, the system is configured to provide an audible and/or visual alert indicating that patient temperature is outside of a specified range. In certain embodiments, detailed error information is displayed on a display device.

In certain embodiments, the temperature management system is configured to receive a target patient temperature from a health care provider and an actual patient temperature from a temperature probe positioned on or in the patient. In certain embodiments, the temperature management system is configured to determine the temperature of the heat transfer medium and/or the flow rate of heat transfer medium through the esophageal heat transfer device needed to achieve the target patient temperature. In certain embodiments, the temperature management system is configured to control the temperature of the heat transfer medium and/or the flow rate of heat transfer medium through the esophageal heat transfer device.

In certain embodiments, the temperature management system is configured to manage core body temperature of a patient. In certain embodiments, the temperature management system is configured to induce systemic hypothermia in a patient. In certain embodiments, the temperature management system is configured to maintain normothermia in a patient. In certain embodiments, the temperature management system is configured to re-warm a patient following systemic hypothermia. In certain embodiments, the temperature management system is configured to induce systemic hyperthermia in a patient. In certain embodiments, the temperature management system is configured to maintain patient temperature within a specified range. In certain embodiments, the temperature management system is configured to maintain patient temperature at a goal temperature. In certain embodiments, the goal temperature includes a range or value that is less than 37° C.; alternatively, less than 36° C.; alternatively, less than 35° C.; alternatively, less than 34° C.; alternatively, less than 33° C. In certain embodiments, the goal temperature includes a range or value that is between about 32° C. and about 37° C.; alternatively, between about 32° C. and about 36° C.; alternatively, between about 32° C. and about 35° C.; alternatively, between about 33° C. and about 36° C.; alternatively, between about 33° C. and about 35° C.; or alternatively, between about 33° C. and about 34° C. In certain embodiments, the temperature management system is configured to alter patient temperature at a specified rate.

In certain embodiments, the temperature management system is configured to maintain patient core body temperature with a maximum variance of about 1.0° C. from a goal temperature. In certain embodiments, the temperature management system is configured to maintain patient core body temperature within about 1.0° C. of a goal temperature. In certain embodiments, the temperature management system is configured to maintain patient core body temperature within about 0.5° C. of a goal temperature.

In certain embodiments, the temperature management system is configured to raise a 70 kg patient's temperature by at least 0.1° C. per hour. In certain embodiments, the temperature management system is configured to raise a 70 kg patient's temperature at a rate between about 0.1° C. per hour and about 1° C. per hour. In certain embodiments, the temperature management system is configured to raise a 70 kg patient's temperature by about 0.1° C. per hour; alternatively, about 0.25° C. per hour; alternatively, about 0.33° C. per hour; alternatively, about 0.5° C. per hour; alternatively, about 0.66° C. per hour; alternatively, about 0.75° C. per hour; or alternatively, about 1° C. per hour.

In certain embodiments, the temperature management system is configured to lower a 70 kg patient's temperature by at least 1° C. per hour. In certain embodiments, the temperature management system is configured to lower a 70 kg patient's temperature at a rate between about 1° C. per hour and about 4° C. per hour. In certain embodiments, the temperature management system is configured to lower a 70 kg patient's temperature by about 1° C. per hour; alternatively, about 1.5° C. per hour; alternatively, about 2° C. per hour; alternatively, about 2.5° C. per hour; alternatively, about 3° C. per hour; alternatively, about 3.5° C. per hour; alternatively, about 4° C. per hour. In certain embodiments, the temperature management system is configured to maintain a 70 kg patient's temperature (+/−1° C.) at a set point between 33° C. and 37° C.

In certain embodiments, the temperature management system is configured to communicate data to a central computer or network of computers. In certain embodiments, the data includes patient temperature, rate of change of patient temperature, oxygen saturation measurements, heat transfer medium flow rate; rate of change of heat transfer medium flow rate; heat transfer medium temperature; and/or heat transfer medium temperature differential after circulating through the heat transfer device. In certain embodiments, the heat transfer medium temperature differential is determined by determining the temperature of the heat transfer medium entering the heat transfer device ("$T_{inlet}$"), determining the temperature of the heat transfer medium exiting the heat transfer device ("$T_{outlet}$"), and determining the difference between $T_{inlet}$ and $T_{outlet}$.

In certain embodiments, the temperature management system enables reprogramming by an operator. In certain embodiments, the temperature management system enables remote reprogramming by an operator. In certain embodiments, the temperature management system is configured for remote reconfiguration. For example, in certain embodiments, software updates are downloaded to the temperature management system from a remote computer or network.

Certain example embodiments of the presently described technology now will be described with respect to the appended figures; however, the scope of the present technology is not intended to be limited thereby. It is to be understood that the scope of the present technology is not to be limited to the specific embodiments described herein. The technology may be practiced other than as particularly described and still be within the scope of the claims.

FIG. 1 shows exemplary components of a temperature management system in accordance with a specific embodiment of the present technology.

The components of the system shown in FIG. 1 include heat exchanger 102, adapter 104, reservoir 106, intake tube 108, output tube 110, auxiliary tubes 112 and 114, temperature probe 116, power cord/plug 118, and optional insulating container 120.

Heat exchanger 102 includes an adapter 104. Adapter 104 is a screw-cap adapter that can be attached to reservoir 106. Adapter 104 includes internal threads for attaching adapter 104 to the threaded neck of reservoir 106. Adapter 104 includes intake tube 108 and output tube 110. Intake tube 108 extends towards and terminates adjacent the bottom of reservoir 106. Auxiliary tubes 112 and 114 are connected to heat exchanger 102 and extend to a heat transfer device (not shown). As shown by the directional indicators, auxiliary tube 114 carries heat transfer medium from heat exchanger 102 to the heat transfer device and auxiliary tube 112 carries heat transfer medium from the heat transfer device back to heat exchanger 102. In certain embodiments, the heat transfer device is capable of being placed in a patient's esophagus. Temperature probe 116 interfaces with heat exchanger 102. The distal end of temperature probe 116 can be placed on or in a patient to monitor patient temperature. In certain embodiments, temperature probe 116 is a gastric temperature probe that is positioned within a patient's stomach. Power to heat exchanger 102 is obtained from the mains power supply via power cord/plug 118.

Figure 2:
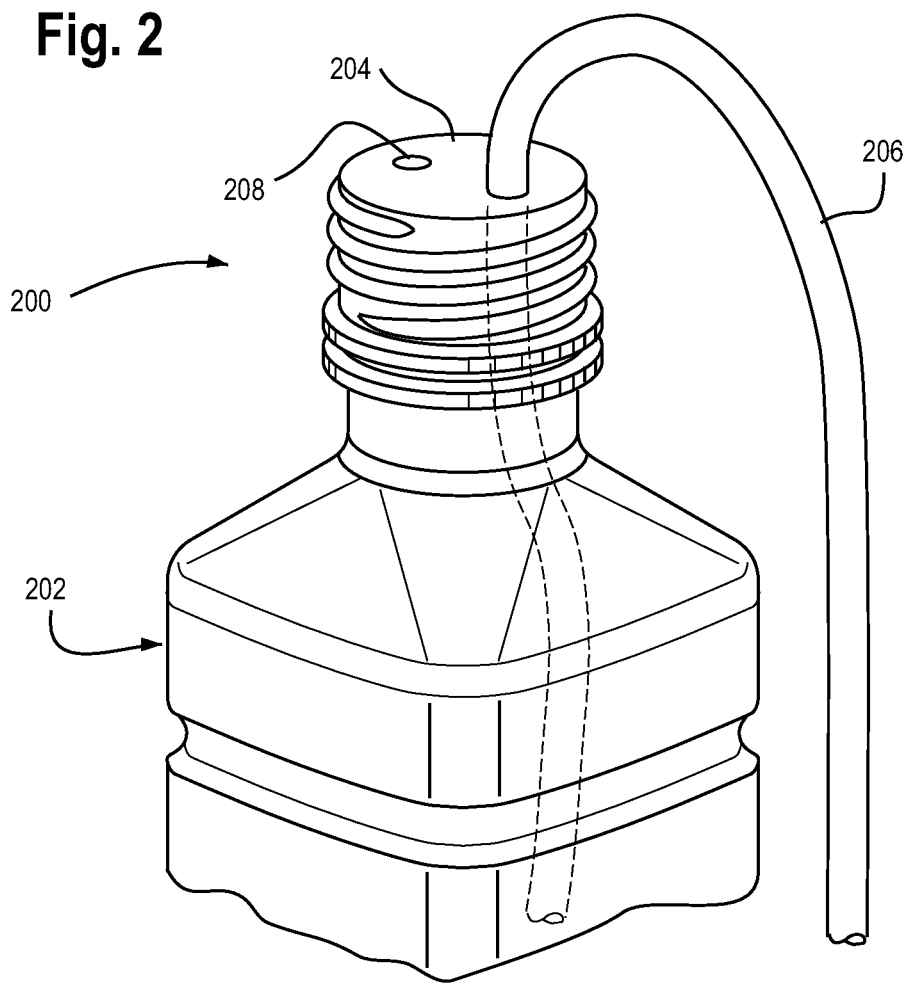
FIG. 2 depicts a schematic representation of an adapter attached to a reservoir in accordance with another embodiment of the present technology.

FIG. 2 shows exemplary components of a temperature management system 200 in accordance with a specific embodiment of the present technology. In particular, FIG. 2 shows an adapter 204 attached to a reservoir 202. Adapter 204 can be fitted within an opening in reservoir 202 (e.g., the mouth of reservoir 202). Alternatively, adapter 204 can be a screw cap that is affixed to the threaded neck of reservoir 202. Adapter 204 contains one or more reservoir access ports 208. In one embodiment, intake tube 206 runs through a reservoir access port 208. Intake tube 206 enters reservoir 202 via one such access port. Intake tube 206 extends towards and terminates adjacent the bottom of reservoir 202.

In certain embodiments, an output tube (not shown) runs through a reservoir access port 208. In certain embodiments, at least one of the one or more reservoir access ports 208 serves as a vent.

Figure 3:
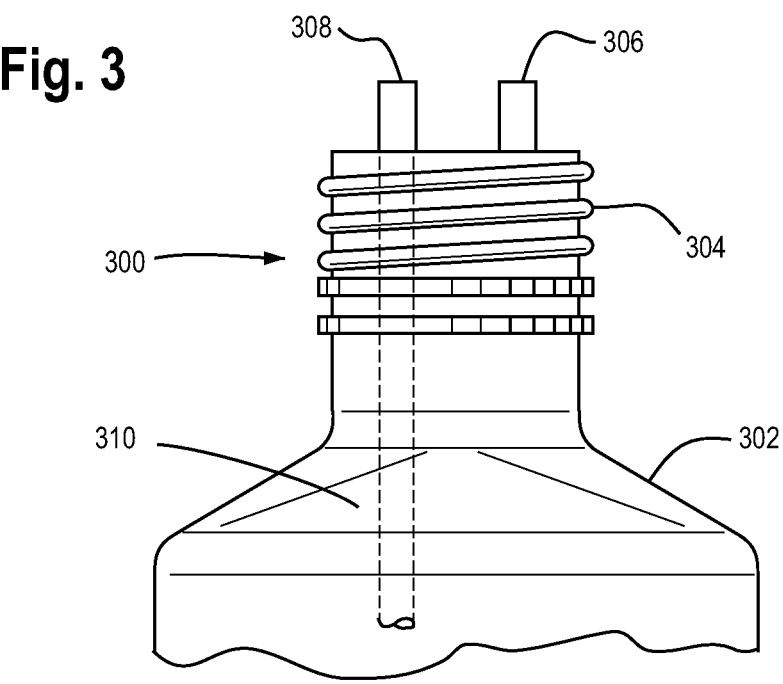
FIG. 3 depicts a schematic representation of an adapter attached to a reservoir in accordance with another embodiment of the present technology.

FIG. 3 shows exemplary components of a temperature management system 300 in accordance with another specific embodiment of the present technology. In particular, FIG. 3 shows an adapter 304 attached to a reservoir 302. Adapter 304 can be fitted within an opening in reservoir 302. Alternatively, adapter 304 can be a screw cap that is affixed to the threaded neck of reservoir 302. An extension tube (not shown) connects to a fitting 308 which in turn is held in adapter 304. Fitting 308 connects with an intake tube 310 that extends towards and terminates adjacent the bottom of reservoir 302. An output tube (not shown) is detachably connected via a fitting 306 in adapter 304.

Figure 4B:
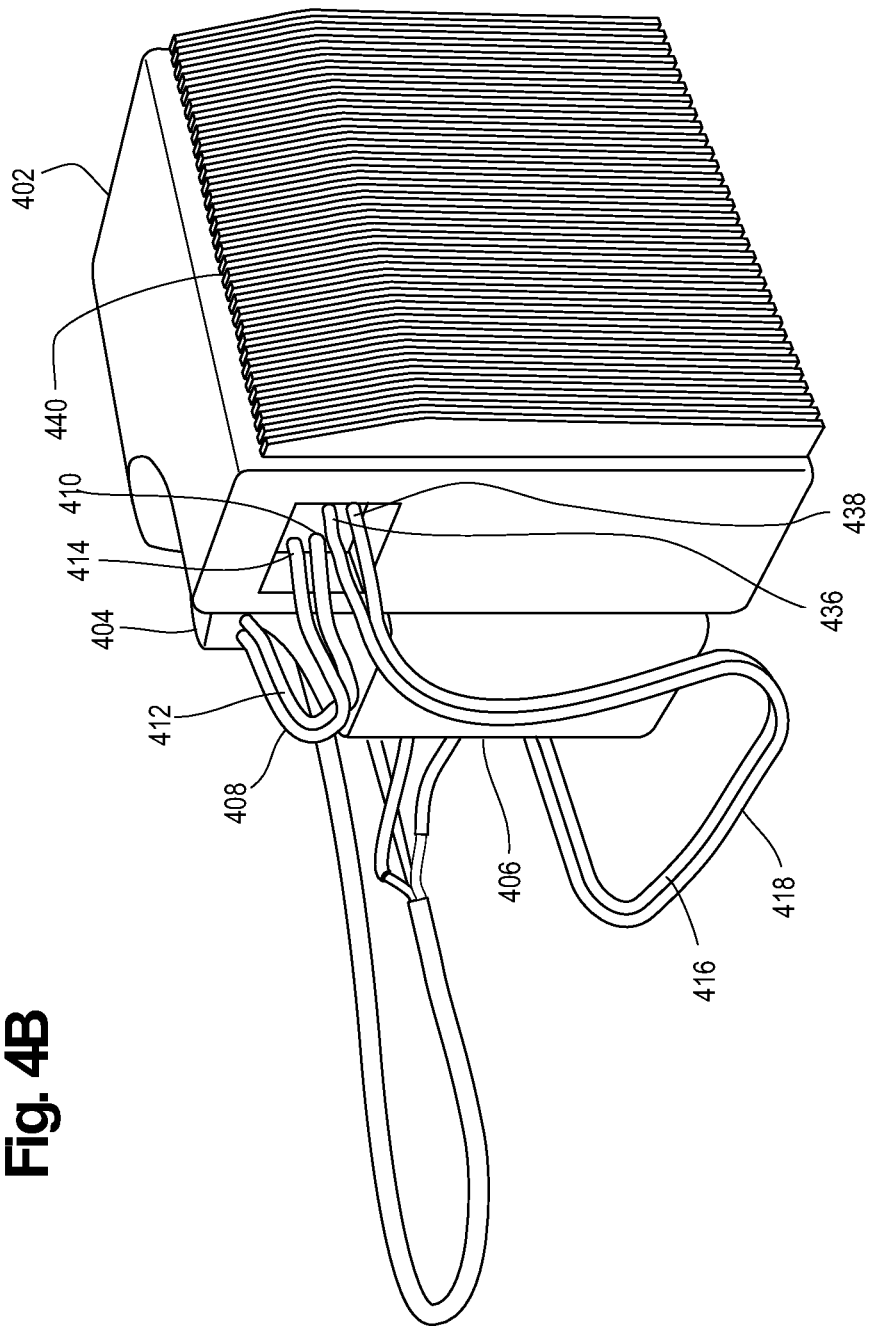

FIGS. 4A and 4B show exemplary components of a temperature management system in accordance with a specific embodiment of the present technology.

The components of the system shown in FIG. 4A include heat exchanger 402, adapter 404, reservoir 406, intake tube 408, output tube 412, esophageal heat transfer device 420, operator interface 422, patient input port 424, temperature probe 426, auxiliary port 428, pulse oximeter 430, plug 432, and insulating container 434. Additional components of the system shown in FIG. 4B include intake tube port 410, output tube port 414, auxiliary tubes 416 and 418, auxiliary tube ports 436 and 438 and vented panel 440.

Reservoir 406 is connected to adapter 404. In certain embodiments, adapter 404 includes a screw-top or snap-on cap. Intake tube 408 extends from adapter 404 and is connected to heat exchanger 402 at intake tube port 410. Intake tube 408 delivers heat transfer medium from reservoir 406 to heat exchanger 402. Output tube 412 extends from adapter 404 and is connected to heat exchanger 402 at output tube port 414.

Auxiliary tubes 416 and 418 are connected to heat exchanger 402 via auxiliary tube ports 436 and 438, respectively, and extend to esophageal heat transfer device 420. Heat exchanger 402 includes operator interface 422. In certain embodiments, operator interface 422 includes a display device and/or one or more knobs or buttons that enable the operator to manipulate certain settings of one or more components of the temperature management system.

Temperature probe 426 connects to heat exchanger 402 via patient input port 424. In certain embodiments, the distal end of temperature probe 426 is placed on or in a patient to monitor patient temperature. In certain embodiments, temperature probe 426 is a gastric temperature probe that is positioned within a patient's stomach. In certain embodiments, another patient input device, such as pulse oximeter 430, connects to heat exchanger 402 via auxiliary port 428. In certain embodiments, pulse oximeter 430 is a transmissive pulse oximeter. In certain embodiments, pulse oximeter 430 is a reflectance pulse oximeter. In certain embodiments, pulse oximeter 430 senses oxygen saturation and, optionally, heat rate.

Power to heat exchanger 402 is obtained from a power supply, such as vehicle power or a mains power supply, via plug 432.

Figure 5:
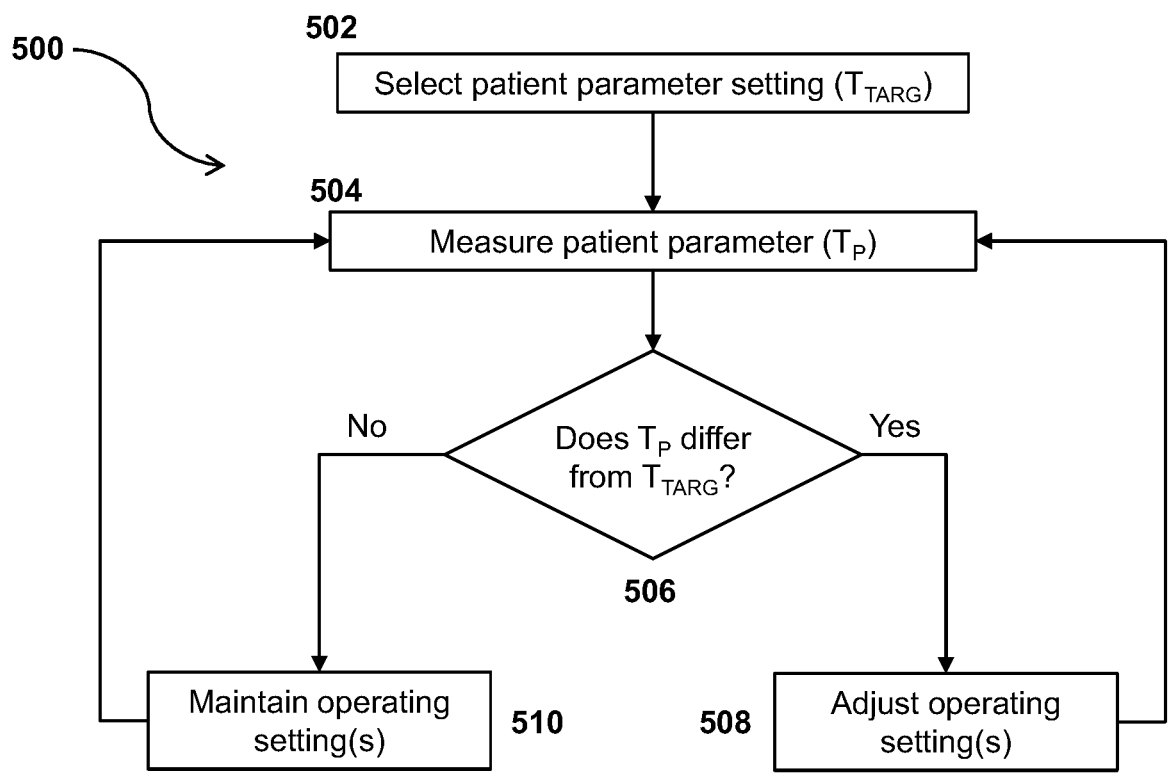
FIG. 5 shows a flowchart of one embodiment of the present technology.

FIG. 5 shows a flow diagram of a method 500 for operating a temperature management system in accordance with a specific embodiment of the present technology. According to various embodiments, at least a portion of the activity described with respect to FIG. 1 may be implemented via one or more temperature management systems described herein.

As shown at 502, a temperature management system enables an operator (e.g., EMS personnel) to set or select an initial setting for one or more patient parameters. In certain embodiments, the patient parameters include a target patient temperature and/or rate of patient temperature change. In certain embodiments, the patient parameter is a target patient temperature. In certain embodiments, the target patient temperature is a threshold value or a range. In certain embodiments, the target patient temperature includes an upper and/or a lower limit. In certain embodiments, the target patient temperature is a value or range between 33° C. and 37° C. For example, in certain embodiments, an operator employs an operator interface of a temperature management system to select a target patient temperature of 34° C. During the period of temperature management, the setting may be adjusted manually or automatically, as further described herein.

In certain embodiments, the setting specifies a temperature management protocol. In certain embodiments, the temperature management protocol includes one or more cycles. For example, in certain embodiments, the setting specifies a hypothermia protocol. In certain embodiments, the hypothermia protocol includes a cooling cycle and a re-warming cycle. In certain embodiments, the cooling cycle lasts between about 12 and about 48 hours. In certain embodiments, the cooling cycle lasts for at least 24 hours. In certain embodiments, the cooling cycle lasts for about 24 hours.

A patient parameter, such as actual patient temperature ($T_P$), is measured, as indicated by block 504. In certain embodiments, $T_P$ is measured via a temperature probe. In certain embodiments, $T_P$ is measured using a thermistor that converts temperature to electrical resistance. In certain embodiments, $T_P$ is continuously measured. In certain embodiments, $T_P$ is measured periodically. In certain embodiments, a value for $T_P$ is displayed on a user interface of the temperature management system.

As indicated by decision diamond 506, the temperature management system compares the target patient temperature to $T_P$. In certain embodiments, $T_P$ is a single measurement taken at a discrete point in time. In certain embodiments, $T_P$ is a mean temperature obtained over a period of time.

If $T_P$ differs from the target patient temperature, then the temperature management system adjusts one or more operational settings of the temperature management system, as indicated by block 508. If $T_P$ does not differ from the target patient temperature, then the temperature management system maintains one or more operational settings of the temperature management system, as indicated by block 510. In certain embodiments, the operational settings include a temperature and/or a flow rate of a heat transfer medium. In certain embodiments, the operational setting is a temperature of the heat transfer medium. In certain embodiments, the operational setting is a flow rate of the heat transfer medium.

Figure 6A:
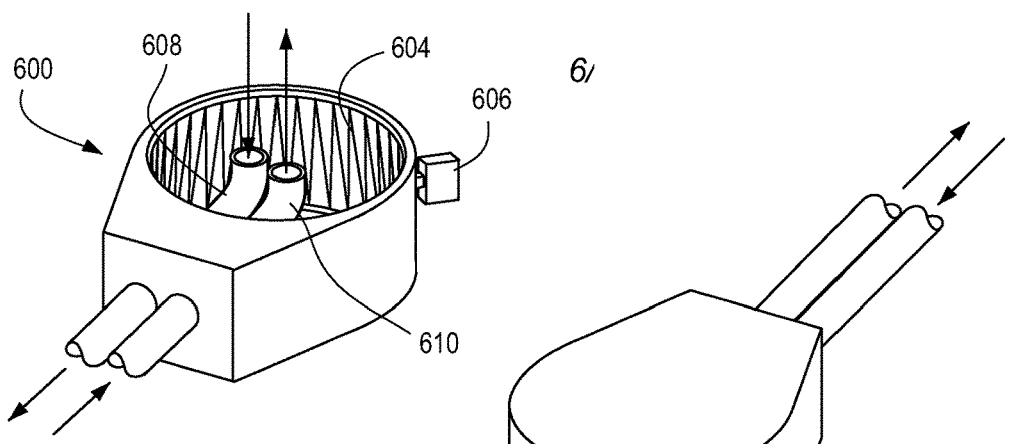
FIGS. 6A and 6B show views of one embodiment of an adapter for connecting a reservoir to a heat exchanger according to the present technology.
Figure 6B:
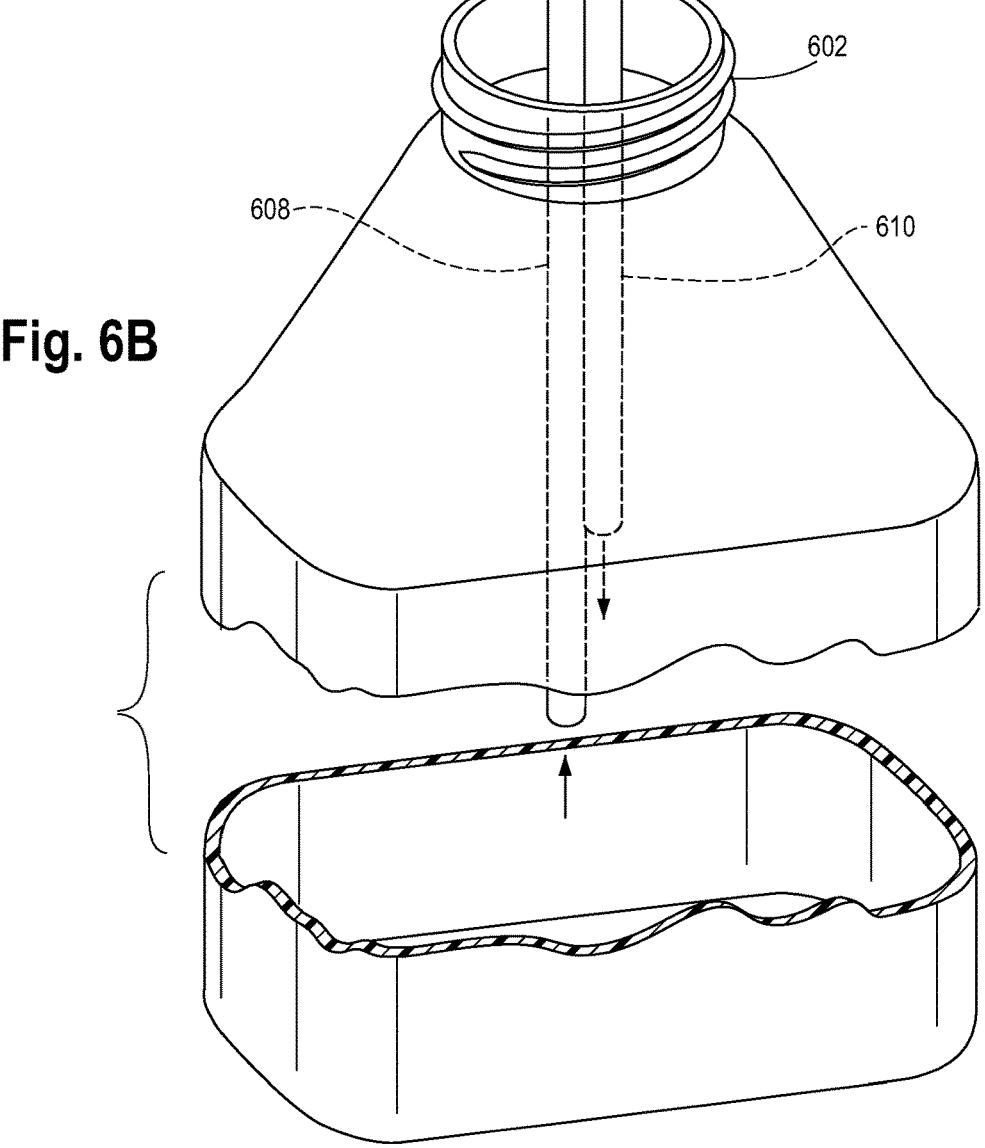

FIGS. 6A and 6B show an exemplary adapter 600 for connecting a reservoir 602 to a heat exchanger (not shown) in accordance with a specific embodiment of the present technology.

Adapter 600 includes compression seal 604 and lever 606. Manual displacement of lever 606 loosens and/or tightens compression seal 604.

Adapter 600 includes intake tube 608. When adapter 600 is attached to a reservoir, such as reservoir 602, intake tube 608 extends into and contacts heat transfer medium in the reservoir. In certain embodiments, intake tube 608 extends towards and terminates adjacent the bottom of reservoir 602.

Adapter 600 also includes output tube 610 for returning spent heat transfer medium to the reservoir.

Example 1

In order to achieve a desired temperature change per unit time, a heat exchanger of the present technology has sufficient heating and cooling capacity. The mechanism of heat transfer into or out of the patient is similar for both the heating and cooling case.

For a thermal system:

$$\frac{dQ}{dt} = mCp\frac{dTp}{dt},$$

where:
Q=Heat energy transferred from patient (J)
Cp=thermal capacitance of the patient (J/kg° K)
m=patient mass 165 lbs (75 kg)

$$\frac{dTp}{dt} = \text{Rate of Change of } Temp\ (°\ C./s)$$

In this example, the average thermal capacitance of a patient, which is 3470 J/kg° K, can be used. Therefore, at a targeted cooling rate of 1.0° C./hour, 72 W of cooling are required. Similarly for a rate of temperature rise of 0.1° C./hour, 7.2 W of warming are required.

Parasitic system effects will occur, such as heat lost or gained through the auxiliary tube set, and/or convective or conductive losses around other system components. Accordingly, a suitable load factor may be applied to the system to ensure that it will be effective.

In addition, the heat exchanger should have the capacity to cool the heat transfer medium to as low a temperature as practicable to maximize the heat transfer effects in the heat transfer device. For example, in the case of a water-based heat transfer medium, which will start to freeze near 0° C., a temperature of 4° C. may be chosen as the desired low temperature for the heat transfer medium.

Thus, if a load factor of 300% is applied to the cooling capacity calculated in this example, the heat exchanger has a cooling capacity of at least 216 W while circulating 4° C. coolant.

Example 2

A Gaymar Medi-Therm III (Model MTA7900) chiller was set up in standard fashion to perform temperature management of a patient. A simulated patient was utilized consisting of an insulated body of water, weighing approximately 20 kg, at baseline temperature of approximately 37° C. An exemplary esophageal cooling device was connected to the Medi-Therm chiller, with the addition of in-line connectors to allow for thermocouple placement into the inlet and outlet streams of coolant through the esophageal cooling device. After turning on the Medi-Therm III and setting goal patient temperature to 37° C., a steady state was reached with coolant temperature equal to simulated body temperature (37° C.). At this point, $T_{inlet}$ was equal to $T_{outlet}$, giving a delta T of 0. To determine the maximum delta T, the entire esophageal cooling device was submerged into the simulated patient and the Medi-Therm was set to cooling mode, with the coolant set point set to the coldest option (4° C.). As the coolant temperature decreased from 37° C., delta T was observed to increase from zero, to a maximum of 1.1° C., at the point that coolant temperature was 10° C., and simulated body temperature was 36.6° C. Therefore, the efficiency of the esophageal cooling device is unexpectedly high, while the capacity of the Gaymar Medi-Therm III chiller is unexpectedly oversized. In certain embodiments, the desired temperature change in a patient can be achieved with as little as about 75 W of heat extraction. Thus, in certain embodiments, a 100 W chiller would be sufficient to effect the desired temperature change.

In certain embodiments, the term "patient" refers to a mammal in need of therapy for a condition, disease, or disorder or the symptoms associated therewith. The term "patient" includes dogs, cats, pigs, cows, sheep, goats, horses, rats, mice and humans. The term "patient" does not exclude an individual that is normal in all respects.

In the preceding paragraphs, temperature is expressed in degrees Celsius. It should be understood that temperature may be expressed in a different manner, such as degrees Fahrenheit or Kelvin.

In the preceding paragraphs, use of the singular includes the plural except where specifically indicated. As used herein, the words "a," "an," and "the" mean "one or more," unless otherwise specified. In addition, where aspects of the present technology are described with reference to lists of alternatives, the technology includes any individual member or subgroup of the list of alternatives and any combinations of one or more thereof.

The disclosures of all patents and publications, including published patent applications, are hereby incorporated by reference in their entireties to the same extent as if each patent and publication were specifically and individually incorporated by reference.

It is to be understood that the scope of the present technology is not to be limited to the specific embodiments described above. The present technology may be practiced other than as particularly described and still be within the scope of the accompanying claims.

The presently described technology is now described in such full, clear, concise and exact terms as to enable any person skilled in the art to which it pertains, to practice the same. The foregoing description of the present technology provides illustration and description, but is not intended to be exhaustive or to limit the technology to the precise one disclosed. Modifications and variations are possible in light of the above teachings or may be acquired from practice of the technology. Thus, it is noted that the scope of the invention is defined by the claims and their equivalents. Therefore, it is to be understood that the foregoing describes preferred embodiments of the technology and that modifications may be made therein without departing from the spirit or scope of the invention as set forth in the appended claims and their equivalents.

The invention claimed is:

1. A portable temperature management system, the system comprising:
   (a) an esophageal heat transfer device including at least one lumen that provides a flow path for a heat transfer medium and a heat transfer region, wherein the heat transfer region has a diameter of about 1.0 to about 2.0 centimeters and a length of about 30 to about 60 centimeters;
   (b) a reservoir for storing the heat transfer medium;
   (c) a heat exchanger configured to regulate temperature of the heat transfer medium, wherein the heat exchanger comprises a pump for circulating the heat transfer medium along the flow path; and (d) a power source contained within the heat exchanger, the power source comprising one or more batteries; and (e) an adapter for coupling the reservoir to the heat exchanger, wherein the adapter includes a compression seal and a lever for loosening and tightening the compression seal, wherein the lever is configured to move along a partially circumferential path about the compression seal to tighten the compression seal when coupling the reservoir to the adapter.

2. The system of claim 1, wherein the reservoir is disposable.

3. The system of claim 1, wherein the heat exchanger occupies less than 9000 cm$^3$ of space.

4. The system of claim 1, wherein the heat exchanger occupies less than 7000 cm$^3$ of space.

5. The system of claim 1, further comprising at least one tube for connecting the heat exchanger to the esophageal heat transfer device.

6. The system of claim 1, further comprising:

(e) at least one processor;

(f) at least one operator interface configured to provide input to the processor;

(g) at least one input device; and (h) at least one memory device that stores a plurality of instructions, which when executed by the at least one processor, cause the at least one processor to:

(i) operate with the at least one operator interface to receive a criterion for a feedback parameter;

(ii) operate with the at least one input device to receive a measured value for the feedback parameter;

(iii) determine whether the measured value satisfies the criterion; and (iv) adjust an operational setting of the system when the measured value does not satisfy the criterion.

7. The system of claim 6, wherein the feedback parameter is patient temperature.

8. The system of claim 7, wherein the criterion for patient temperature is a temperature range.

9. The system of claim 8, wherein the temperature range is between about 33° C. to about 36° C.

10. The system of claim 6, wherein the operational setting is a temperature of the heat transfer medium or a flow rate of the heat transfer medium.

11. The system of claim 6, wherein the feedback parameter is a heat transfer medium temperature differential.

12. The system of claim 11, wherein the heat transfer medium temperature differential is determined by (1) obtaining a first temperature of the heat transfer medium;

(2) obtaining a second temperature of the heat transfer medium; and (3) ascertaining a difference between the first temperature and the second temperature.

13. The system of claim 1, wherein the heat transfer region has a surface area from about 100 cm$^2$ to about 350 cm$^2$.

14. The system of claim 1, wherein the esophageal heat transfer device holds between about 0.02 liters and about 0.1 liters of heat transfer medium.

15. The system of claim 1, wherein the reservoir holds between about 1 liter of heat transfer medium and about 3 liters of heat transfer medium.

16. The system of claim 1, wherein the power source comprises a rechargeable battery.

17. The system of claim 1, wherein the heat transfer region is a non-inflatable heat transfer region.

\* \* \* \* \*